United States Patent [19]

Uetake et al.

[11] Patent Number: 4,922,904
[45] Date of Patent: May 8, 1990

[54] APPARATUS FOR CONNECTING THREAD TO SURGICAL NEEDLE

[75] Inventors: Tsuyoshi Uetake; Iwao Ueno, both of Tokyo, Japan

[73] Assignee: Keisei Medical Industrial Company Limited, Tokyo, Japan

[21] Appl. No.: 363,533

[22] Filed: Jun. 8, 1989

[30] Foreign Application Priority Data

Jun. 18, 1988 [JP] Japan ................... 63-150798

[51] Int. Cl.$^5$ ............ A61B 17/06; B21D 39/00; B41G 1/06
[52] U.S. Cl. ........................... 606/226; 29/517; 163/1; 163/5
[58] Field of Search ............ 128/339; 29/517, 782, 29/788, 819; 163/1, 5

[56] References Cited

U.S. PATENT DOCUMENTS

| | | | |
|---|---|---|---|
| 2,411,079 | 11/1946 | Baule | 128/339 |
| 3,611,551 | 10/1971 | Shave et al. | 128/339 |
| 3,835,912 | 9/1974 | Kristensen | 128/339 |
| 3,910,282 | 10/1975 | Messer et al. | 128/339 |
| 4,072,041 | 2/1978 | Hoffman et al. | 72/416 |
| 4,722,384 | 2/1988 | Matsutani | 163/1 |
| 4,805,292 | 2/1989 | Noguchi | 29/445 |

Primary Examiner—Edward M. Coven
Assistant Examiner—Gary Jackson
Attorney, Agent, or Firm—Peter J. Georges

[57] ABSTRACT

An apparatus for connecting a thread wound on a bobbin to a surgical needle including feeding rollers for unwinding the thread from the bobbin, a tube-like chuck for selectively fix the thread thereto, a guide for guiding the front end of the thread, a feeding device for supporting the needle such that a hole formed in a rear end face of the needle is faced to the front end of the thread, and a clamping device having pushing rods for pressing the rear end of the needle to clamp the thread in the hole. By moving the needle to the guide, the front end of the thread is inserted into the hole of the needle, and then the clamping device is driven to press the rear end of the needle so that the thread is clamped in the hole. Then, the thread is unwound from the bobbin by a desired length by moving the feeding device away from the guide, and finally the thread is cut along an inclined line.

11 Claims, 6 Drawing Sheets

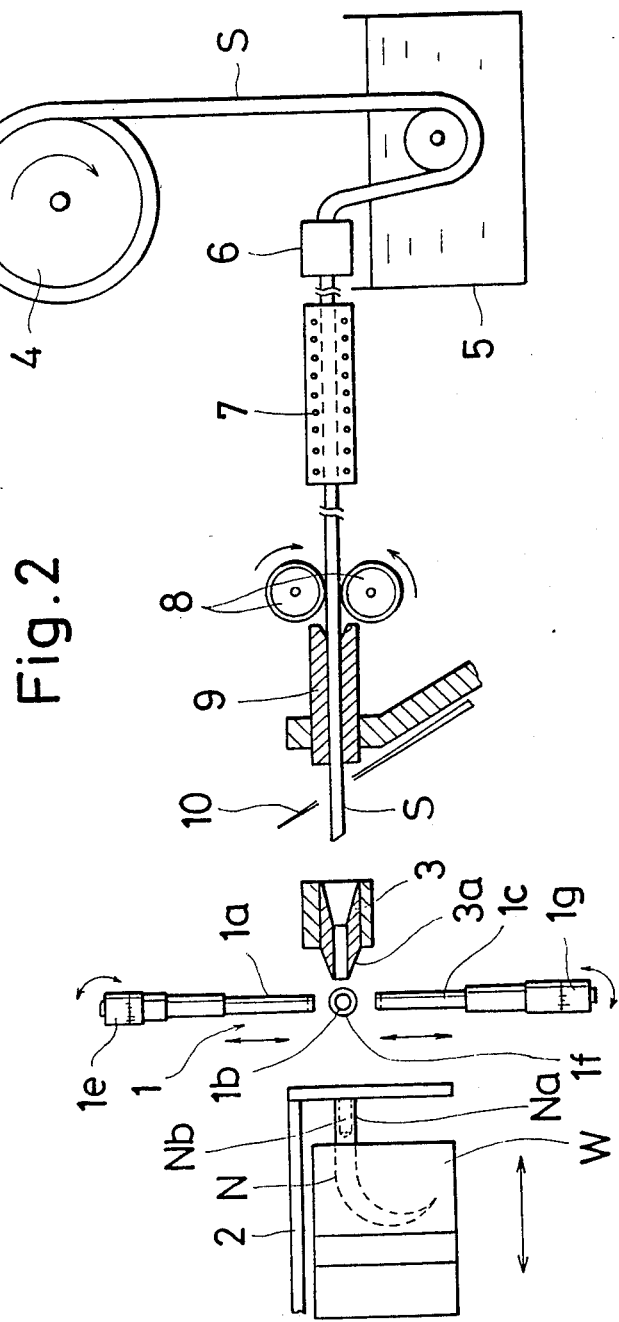
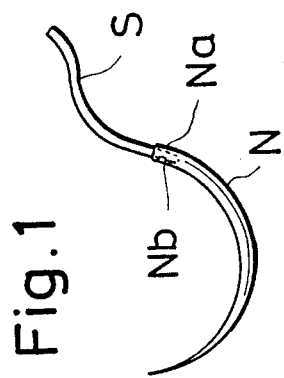

4,922,904

APPARATUS FOR CONNECTING THREAD TO SURGICAL NEEDLE

BACKGROUND OF THE INVENTION

1. Field of the Invention

The present invention relates to an automatic apparatus for connecting a thread to a surgical needle by inserting a front end of the thread into a hole formed in a rear end of the needle and then pressing the rear end of the needle to clamp the thread in the hole of the needle.

2. Related Art Statement

In the surgical operation, there have been widely used surgical needles having threads previously connected to the needles in order to connect parts of a patient body. There are prepared a quite large kinds of the surgical needles, and some of them have very small diameters such as 1 mm or less. It should be noted that threads to be connected to such thin needles have also very small diameters.

There have been developed various methods for connecting the threads to the surgical needles, and in the view point of the facileness in use, a surgical needle having a thread clamped in a hole formed in the rear end of needle has been preferably used. FIG. 1 illustrates such a surgical needle. In case of connecting a thread S to a surgical needle N, a front end of thread is manually inserted into a hole Nb formed in an end face of a rear end Na and then the rear end Na of the needle is pressed with the aid of a clamping machine to clamp the front end of thread S in the hole Nb. During this manual operation, an operator watches the thread S and needle N under a microscope. It is apparent that this connecting method requires an experience of labors and further the efficiency of the work is very low. Therefore, the manufacturing cost of the surgical needle is liable to be increased and possibility of occurrence of unusable needles in large. Moreover, since the operation has to be effected by inspecting the front end of thread S and the rear end Na of needle N under the microscope or magnifier, the eyes of the workers might be fatigued to a large extent.

SUMMARY OF THE INVENTION

The present invention has for its object to provide a novel and useful apparatus for automatically connecting a surgical thread to a surgical needle by means of which the thread can be coupled with the rear end of needle in an efficient and reliable manner.

It is another object of the invention to provide an apparatus for automatically connecting a surgical thread to a rear end of surgical needle in which a length of the thread can be determined at will.

According to the invention, an apparatus for automatically connecting a surgical thread to a surgical needle having a hole formed in an end face of a rear end thereof, comprises a means for feeding the surgical needle into a given position;

a means for supplying the surgical thread;

a means for guiding a front end of the surgical thread into a given position at which the front end of surgical thread is faced to an opening of the hole formed in the end face of the rear end of the surgical needle;

a means for inserting the front end of the surgical thread into the hole of the surgical needle;

a means for pressing the rear end of the surgical needle to clamp the front end of the surgical thread in the hole of the rear end of the surgical needle; and a means for cutting the surgical thread at a given point to form the surgical needle having the surgical thread of given length connected to the rear end thereof.

In a preferable embodiment of the apparatus according to the present invention, the surgical thread is wound on a supply reel and is unwound therefrom and there is provided a heating means for heating the thread unwound from the reel to correct a curved shape of the thread into a straight shape.

In another preferable embodiment of the apparatus according to the invention, there are provided a means for pulling the thread after the thread is secured to the needle and a means for confirming whether the thread has been firmly connected to the needle or not.

BRIEF DESCRIPTION OF THE DRAWINGS

FIG. 1 is a plan view showing the surgical needle having the thread connected thereto;

FIG. 2 is a schematic view illustrating a first embodiment of the apparatus according to the invention;

DESCRIPTION OF THE PREFERRED EMBODIMENT

Figure 3:
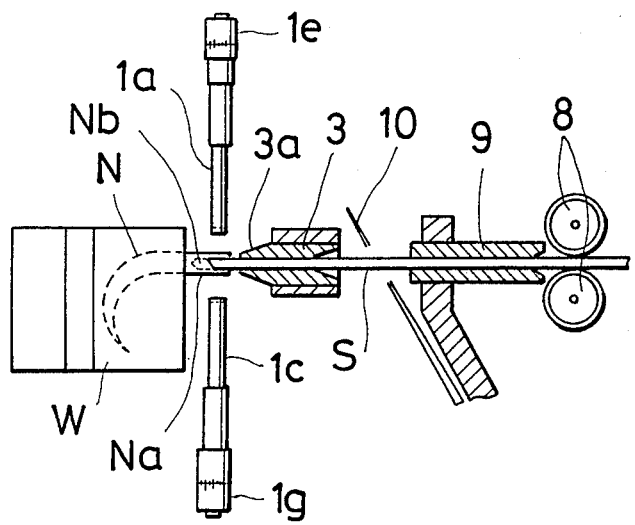
FIG. 3 is a schematic view depicting the operation for inserting the thread into the hole of the needle.

FIG. 2 is a schematic view showing a first embodiment of the apparatus according to the invention. In FIG. 2, a reference numeral 1 denotes a clamping device having four pushing rods 1a, 1b, 1c and 1d (in the drawing the dice 1d is not shown) for clamping a rear end Nb of a surgical needle N after a front end of a thread S has been inserted into a hole Na formed in the end face of the rear end of the surgical needle, so that the thread is fixed to the surgical needle. The four pushing rods 1a to 1d are symmetrically arranged about a longitudinal axis of the thread S so that the hole Nb of the needle is clamped evenly from four mutually perpendicular directions. The stroke of each pushing rods 1a to 1d can be adjusted with the aid of micrometers 1e to 1h, respectively. The needle N is held by a work W and the work is fed by a feeding device 2 having a guide table. The work W is so positioned that the rear end Na of the needle N is aligned with a center of the four pushing rods 1a to 1d. A first guide 3 for guiding the thread S is formed as a thin tube having a tip 3b being aligned with the rear end Na of the needle N. The other end of the tube-like guide 3 has a tapered opening so that the front end of a thread S can be easily inserted into the guide. The thread S is wound on a bobbin 4 and is unwound therefrom. The unwound thread S is passed through a sterilizing liquid contained in a sterilizing tank 5, a sponge 6 for removing the sterilizing liquid from the thread, a tube-like heater 7 for correcting the curved shape of the thread into a straight shape, a pair of feeding rollers 8 and a second guide 9. The thread S fed from the second guide 9 is inserted into the hole formed in the first guide 3. Between the first and second guides 3 and 9, there is arranged a cutting device 10 such as knife and scissors.

Figure 4:
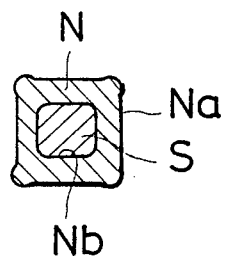
FIG. 4 is a cross sectional view showing the clamped condition.

The thread S is unwound from the bobbin 4 and is immersed into the sterilizing liquid in the tank 5 and is sterilized thereby. Then, the thread S is fed through the heater 7 which includes an electric heating wire and is heated to, for instance 130° to 140° C., so that the curved thread is converted into a straight thread. It should be noted that the temperature of the heater 7 has to be adjusted in accordance with the diameter and material of the thread. The thread S thus processed is further fed toward the clamping device 1, and at the same time the surgical needle N is moved together with the work W toward the first guide 3 such that the rear end Na of the needle N is almost made in contact with the front end 3a of the first guide 3 as illustrated in FIG. 3. That is to say, the hole Nb formed in the rear end Na of the needle N is aligned with the front end opening of the guide 3. Then, the thread S is further fed by means of the rollers 8 and the front end of the thread is inserted into the hole Nb of the needle N via the opening of the first guide 3. next, the pushing rods 1a to 1d of the clamping device 1 are moved toward the needle to press the rear end of the needle and the thread is firmly secured to the needle N as shown in FIG. 4. It should be noted that the circular cross section of the hole Nb is deformed into a substantially square cross section by the clamping operation. The surgical needle N having the thread S connected thereto is then fed in the leftward in FIG. 2 by a given distance by moving the feeding device 2, and after that the thread S is cut by the cutting device 10. In the present embodiment, the thread S is cut along an inclined line, so that the thread has a sharp front end, and this facilitates the inserting operation of the thread into the hole Nb of the needle as well as the hole of the guide 3.

As explained above, with the aid of the apparatus according to the present invention, the fine thread S can be automatically and positively secured to the surgical needle N in a simple and efficient manner. Particularly, in the present embodiment, since the curved thread is first corrected into the straight thread and the front end of the thread is easily and thus correctly inserted into the holes of the needle N and guide 3.

Figure 5:
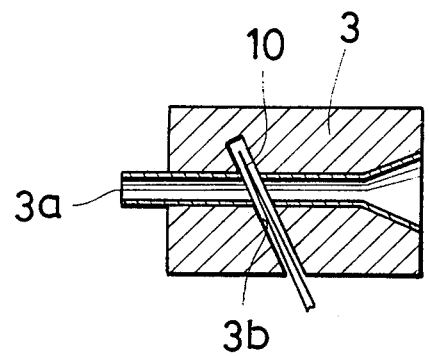
FIG. 5 is a cross sectional view illustrating a modification of the guide shown in FIG. 2.

FIG. 5 is a cross sectional view depicting another embodiment of the first guide 3 according to the invention. In the present embodiment, at a middle of the elongated guide 3 is formed a slit 3b and the cutting blade of the cutting device 10 is inserted into the slit. In the present embodiment, after the front end of the thread S is once cut, the front end of the thread is not exposed out of the guide 3, the obliquely cut front end of the thread is hardly deformed and therefore the operation of inserting the front end of the thread in the hole Nb of the needle N can be carried out much more positively.

Figure 6:
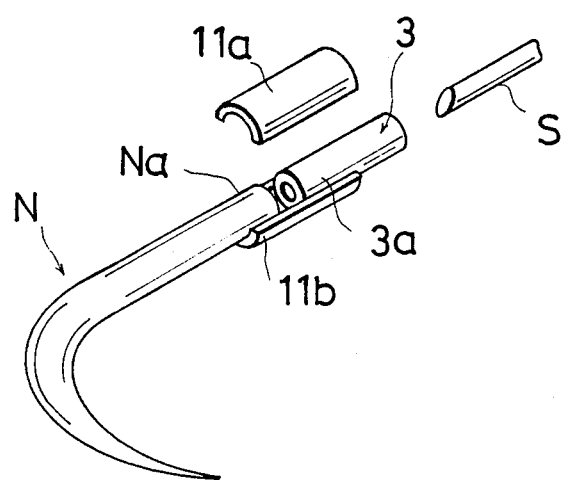
FIG. 6 is a perspective view depicting a centering device according to the invention.

FIG. 6 is a perspective view showing a positioning device for aligning the rear end Na of the needle N with the front end 3a of the first guide 3. The positioning device comprises two semicylindrical members 11a and 11b. The rear end Na of the needle N and the front end 3a of the first guide 3 are clamped between the semicylindrical members 11a and 11b and then, the front end of the thread S is inserted into the hole formed in the end face of the needle. After the centering members 11a and 11b are removed from the needle N and the guide 3, the clamping rods 1a to 1d are moved toward the center axis.

It should be noted that the diameters of the holes formed in the first and second guides 3 and 9 should be matched to the diameter of the thread, and thus these guides have to be changed in accordance with the thread to be used. For this purpose, the whole guides may be exchanged or parts of the guides may be exchanged.

In the embodiment just explained above, the four pushing rods 1a to 1d of the clamping device 1 are moved simultaneously, but opposite pushing rods 1a and 1c may be first moved simultaneously and then the remaining opposite pushing rods 1b and 1d may be simultaneously moved. Moreover, the clamping device 1 may comprise a pair of opposite pushing rods. In this case, after the pushing rods are moved, they may be rotated by 90 degrees about the center axis and then are operated again. Further, the clamping device may include more than four pushing rods and these pushing rods may be moved simultaneously. It should be further noted that the thread may be fed by ejecting an air stream from an air nozzle. The thread may be cut simultaneously with or prior to the clamping operation.

In the above mentioned embodiment, the length of the thread connected to the surgical needle is previously determined and can not be changed easily. In practice, it is often required to use the surgical needle to which the threads having various lengths are connected. According to another aspect of the present invention, the length of thread connected to the needle can be changed easily and precisely.

Figure 7:
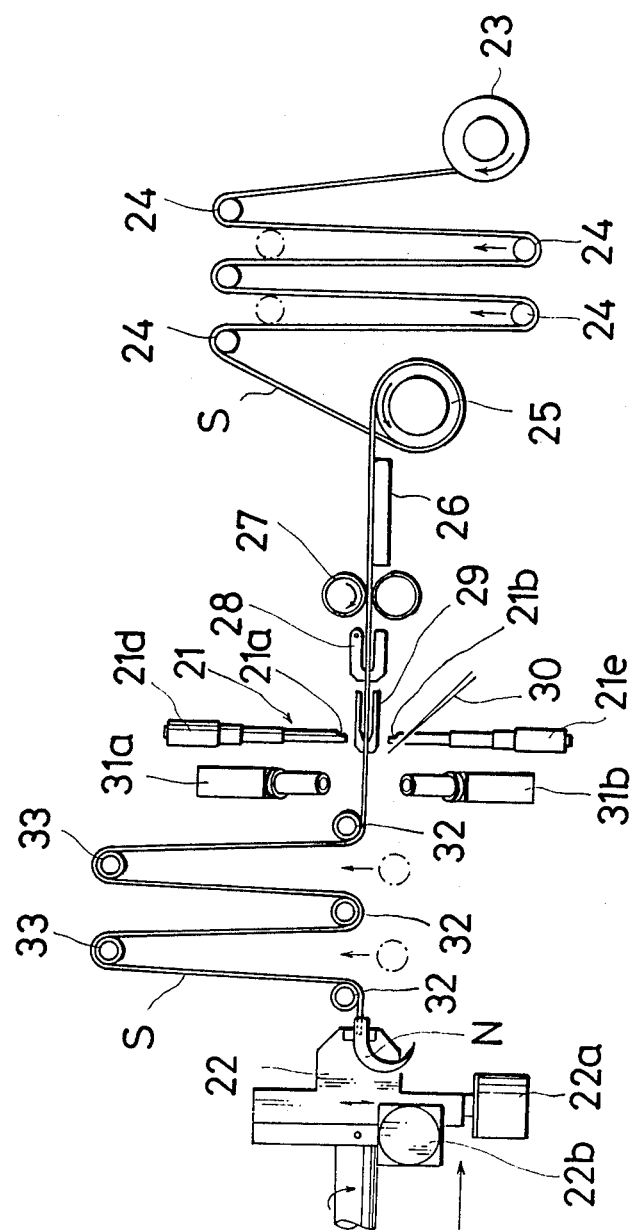
FIG. 7 is a schematic view showing a second embodiment of the apparatus according to the invention.
Figure 8:
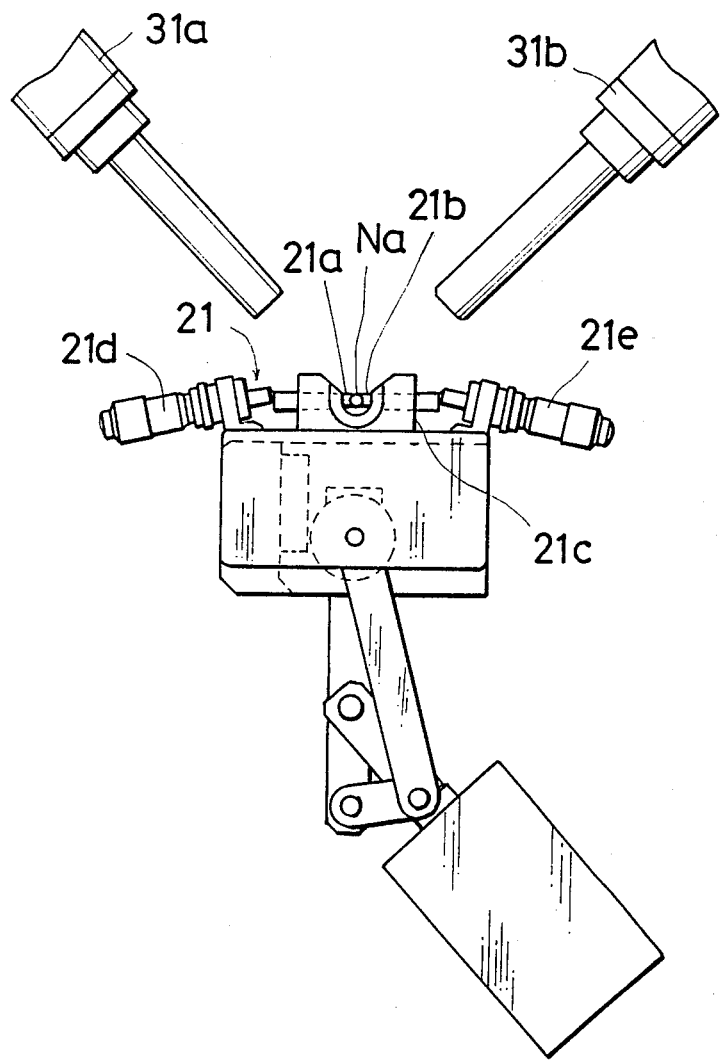
FIG. 8 is a side view illustrating the clamping device shown in FIG. 7.

FIG. 7 is a schematic view showing another embodiment of the apparatus according to the invention. A clamping device is denoted by a reference numeral 21 and includes two pushing rods 21a to 21b. Upon the clamping the clamping device 21 is moved leftward from the position shown in FIG. 7. As illustrated in FIG. 8, the pushing rods 21a and 21b are arranged movably within a guide 21c toward the center axis from opposite directions, so that the rear end Na of the surgical needle N can be pressed to clamp the front end of the thread S within the hole Nb formed in the end face of the needle. Strokes over which the pushing rods 21a and 21b are moved can be adjusted by means of micrometers 21d and 21e, respectively. The surgical needle N is held by a feeding device 22 which can be moved front and rear, up and down and can be rotated by means of motors 22a and 22b. To the feeding device 22 surgical needles can be detachably secured one by one with the aid of a handling apparatus not shown. It should be noted that the needle N is held on the feeding device 22 such that the rear end of the needle N is faced toward the clamping device 21. The thread S is wound on a bobbin 23 and is unwound therefrom. The unwound thread S is fed along a plurality of tension adjusting rollers 24, a brake roller 25 for applying a back tension to the thread, a heater 26 for correcting the curved thread into the straight thread, a pair of encoder rollers 27 to one of which is connected a rotary encoder for measuring a length of the thread to be connected to the needle, a feeding chuck 28 for feeding the thread while the front end of the thread is fixed thereto, and a guide 29. The guide 29 is formed as a tube having a thin hole and is arranged movably in the front and back directions. A front end 29a of the guide 29 is made substantially contact into the hole Nb of the needle N such that the center axis of the front end 29a is aligned with the longitudinal direction of the thread S. Near the front end 29a of the guide 29 is arranged a cutting device 30 for cutting the thread S. At the clamping position there are arranged two television cameras 31a and 31b for monitoring the connection of the thread S and the needle N from the opposite directions. Between the feeding device 22 and the guide 29 there are arranged five rollers 32 and 33. As shown in FIG. 7, the two rollers 33 are arranged between the rollers 32 and are movable in the direction perpendicular to the center axis, so that the length of the thread section situating between the guide 29 and the feeding device 22 can be adjusted over a wide range.

In case of connecting the thread S to the needle N, the thread fixed by the chuck 28 is moved toward the feeding device 22. It should be noted that the front end of the thread S is slightly extended from the guide 29 which is also moved in synchronism with the chuck 28. The chuck 28 and guide 29 are moved such that the front end of the thread S is inserted into the hole Nb formed in the end face of the rear end Na of the needle N. Before inserting the thread into the hole Nb of the needle, it is confirmed whether the thread is aligned with the hole Nb or not with the aid of the television cameras 31a and 31b.

Figure 9:
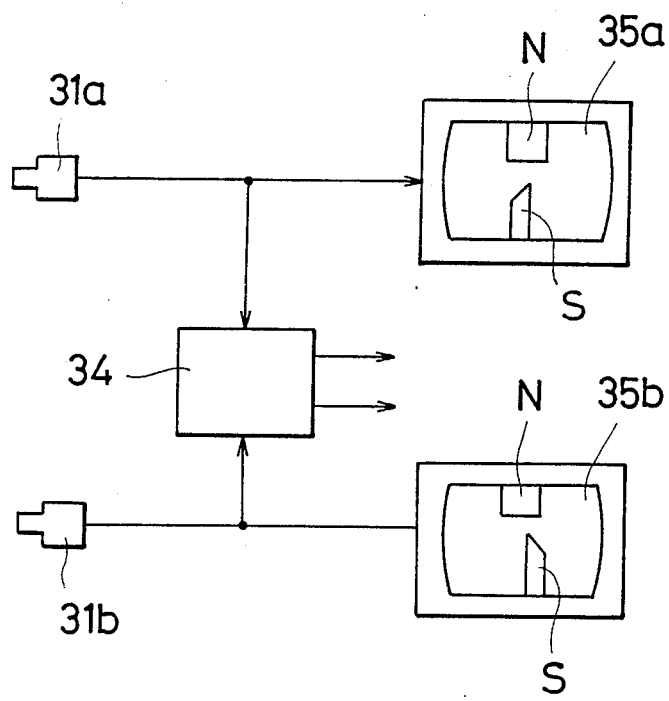
FIG. 9 is a block diagram depicting the monitoring system.

FIG. 9 is a block diagram showing the monitoring system including the television cameras 31a and 31b. The output video signals generated from the television cameras are supplied to a control circuit 34 as well as to display units 35a and 35b, respectively. On the monitor screens of the display units 35a and 35b, there are displayed images of the front end of the thread S and the rear end of the needle N. Since these images are taken from different directions the operator can visually confirm the centering condition. In the control circuit 34, the front edge of the needle N is detected by processing the scanning lines and then the center line of the needle is detected. At the same time, the upper edge of the thread S is detected and then the center line of the thread is detected. Then, the position of the thus detected center lines are compared with each other to detect a deviation between these center lines. The control circuit 34 supplies control signals to the motors 22a and 22b for adjusting the positions of the feeding device 22, i.e. the thread S with respect to the needle N such that the thread is accurately aligned with the needle. In this manner, when the thread is deviated from the hole, one or both of the feeding device 22 and the guide 29 is moved in the direction perpendicular to the center axis until the thread is aligned with the hole. After the front end of the thread S is correctly inserted into the hole Nb of the needle N, the television cameras 31a and 31b are removed from the clamping position and then the clamping device 21 is moved into the clamping position. Next the pushing rods 21a and 21b are simultaneously moved to press the rear end Na of the needle N to deform the hole. Then the feeding device 22 is rotated by 90 degrees about the center axis and the pushing rods 22a and 22b are driven again to press the rear end of the needle. In this manner, the thread S can be secured to the rear end Na of the needle N as shown in FIG. 4.

After the thread has been connected to the needle as explained above, the feeding device 22 is slightly moved in the left-hand direction in FIG. 7 so as to check whether the thread is removed out of the hole of the needle or not by detecting the tension applied to the thread. Then, the chuck 28 releases the thread S and the feeding device 22 is moved into the position illustrated in FIG. 7 to form a space between the feeding device 22 and the guide 29. After that, the rollers 32 and 33 are moved into said space such that the rollers 32 and 33 are positioned on opposite sides of the thread S. Then, the rollers 33 are moved into positions between adjacent rollers 32 to extend the thread S in the zig-zag manner.

In the manner explained above, the thread S is unwound from the bobbin 23 by a desired length. The length of the thread unwound from the bobbin 23 is measured by the rotary encoder coupled with the roller 27 and when a desired length has been unwound, the brake roller 25 is operated to apply the tension to the thread. Then, the movement of the rollers 33 is stopped and thus the unwound operation of the thread is completed. Next the cutting device 30 is driven to cut the thread S. In the manner explained above, threads having different length can be automatically connected to successive needles N in an efficient manner.

In the above mentioned embodiment, the length of the thread S is measured by means of the rotary encoder, but the length of the thread may be measured by detecting the position of the rollers 33. Further, the clamping device 21 may comprise three or four pushing rods. Then, the clamping operation can be effected by one operation as in the case of the first embodiment.

What is claimed is:

1. An apparatus for automatically connecting a surgical thread to a surgical needle having a hole formed in an end face of a rear end thereof, comprising
    a means for feeding the surgical needle into a given position;
    a means for supplying the surgical thread;
    a means for guiding a front end of the surgical thread into a given position at which the front end of surgical thread is faced to an opening of the hole formed in the end face of the rear end of the surgical needle;
    a means for inserting the front end of the surgical thread into the hole of the surgical needle;
    a means for pressing the rear end of the surgical needle to clamp the front end of the surgical thread in the hole of the rear end of the surgical needle; and
    a means for cutting the surgical thread at a given point to form the surgical needle having the surgical thread of a given length connected to the rear end thereof.

2. An apparatus according to claim 1, wherein said means for inserting the front end of the surgical thread into the hole of the surgical needle comprises a tube-like chuck which selectively fixes the thread thereto and is movable in a longitudinal direction of the thread.

3. An apparatus according to claim 1, further comprising a heating means for correcting the curved thread into the straight thread.

4. An apparatus according to claim 1, further comprising a means for sterilizing the thread supplied from the thread supplying means.

5. An apparatus according to claim 1, wherein said cutting means is constructed such that the thread is cut along a line which is inclined with respect to the thread.

6. An apparatus according to claim 1, further comprising a means for confirming whether the thread has been firmly connected to the needle or not by applying a tension to the thread.

7. An apparatus according to claim 1, wherein said needle feeding means is arranged movably in a longitudinal direction, and the apparatus further comprises a means provided between the needle feeding means and the thread guiding means and unwinding the thread from the thread supplying means by a desired length.

8. An apparatus according to claim 7, wherein said unwinding means comprises a first set of rollers arranged on one side of the thread and a second set of rollers arranged on the other side of the thread and movable in a direction perpendicular to the longitudinal direction of the thread between said first set of rollers.

9. An apparatus according to claim 9, further comprising a means arrange between the thread supplying means and the guiding means and applying selectively the brake force to the thread.

10. An apparatus according to claim 1, further comprising a means for monitoring the positions of the hole of the needle and thread prior to insertion of the thread into the hole to derive a deviation signal representing a deviation between the thread and the hole of the needle, and a means for adjusting the relative position between the thread and the hole of the needle in accordance with said deviation signal such that the thread is aligned with the hole of the needle.

11. An apparatus according to claim 10, wherein said monitoring means comprises two television cameras for picking up images of the front end of the thread and the rear end of the needle from different directions.

* * * * *